United States Patent
Spinke et al.

(10) Patent No.: US 7,507,550 B2
(45) Date of Patent: Mar. 24, 2009

(54) ANALYTICAL SANDWICH TEST FOR DETERMINING NT-PROBNP

(75) Inventors: Juergen Spinke, Lorsch (DE); Alfons Nichtl, Hohenpeissenberg (DE); Volker Klemt, Weilheim (DE); Klaus Hallermayer, Feldafing (DE); Michael Grol, Feldafing (DE); Anneliese Borgya, Seeshaupt (DE); Andreas Gallusser, Penzberg (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 0 days.

(21) Appl. No.: 10/994,851

(22) Filed: Nov. 22, 2004

(65) Prior Publication Data

US 2005/0118662 A1 Jun. 2, 2005

(30) Foreign Application Priority Data

Nov. 28, 2003 (DE) ................. 103 55 731

(51) Int. Cl.
| | |
|---|---|
| *G01N 33/53* | (2006.01) |
| *G01N 33/543* | (2006.01) |
| *G01N 33/544* | (2006.01) |
| *G01N 33/545* | (2006.01) |
| *G01N 33/558* | (2006.01) |
| *G01N 33/577* | (2006.01) |
| *G01N 33/551* | (2006.01) |
| *C07K 16/26* | (2006.01) |

(52) U.S. Cl. .............. 435/7.5; 435/7.1; 435/7.92; 435/7.94; 435/7.95; 435/70.21; 435/452; 435/336; 435/287.2; 435/287.9; 436/514; 436/518; 436/524; 436/525; 436/528; 436/531; 436/548; 436/811; 530/324; 530/388.24; 530/389.2; 530/391.1; 530/800; 422/55; 422/56; 422/57; 422/58

(58) Field of Classification Search ............... 435/7.1, 435/7.5, 7.92, 7.94, 7.95, 70.21, 452, 336, 435/287.2, 287.9; 436/514, 518, 524, 525, 436/528, 531, 548, 811; 530/324, 350, 388.24, 530/389.2, 391.1, 800

See application file for complete search history.

(56) References Cited

U.S. PATENT DOCUMENTS

| | | | |
|---|---|---|---|
| 4,861,711 A | 8/1989 | Friesen et al. | |
| 5,073,484 A | 12/1991 | Swanson et al. | |
| 5,141,850 A | 8/1992 | Cole et al. | |
| 5,458,852 A | 10/1995 | Buechler | |
| 5,591,645 A | 1/1997 | Rosenstein | |
| 5,786,163 A | 7/1998 | Hall | |
| 6,117,644 A | 9/2000 | DeBold | |
| 6,461,828 B1 | 10/2002 | Stanton et al. | |
| 6,506,612 B2 | 1/2003 | Kang et al. | |
| 6,833,275 B1 | 12/2004 | Nichtl | |
| 7,109,023 B2 * | 9/2006 | Kang et al. | ............. 435/287.2 |
| 2004/0096920 A1 * | 5/2004 | Davey et al. | ............. 435/7.92 |

FOREIGN PATENT DOCUMENTS

| | | |
|---|---|---|
| EP | 0 291 194 A1 | 11/1988 |
| WO | WO 93/24531 A1 | 12/1993 |
| WO | WO 97/06439 A1 | 2/1997 |
| WO | 00/35951 * | 6/2000 |
| WO | WO 00/45176 A2 | 8/2000 |
| WO | WO 02/083913 A1 | 10/2002 |
| WO | WO 03/087819 A1 | 10/2003 |
| WO | WO 2004/046194 A | 6/2004 |

| WO | WO 2004/099252 A1 | 11/2004 |
| WO | WO 2004/099253 A1 | 11/2004 |

OTHER PUBLICATIONS

Karl et al., 1999. Development of a novel, N-terminal-proBNP (NT-proBNP) assay with a low detection limit. Scand. J. Clin. Lab. Invest. 59 (Suppl. 230): 177-181.*

Omland et al., 2002. N-terminal pro-B-type Natriuretic peptide and long-term mortality in acute coronary syndromes. Circulation 106: 2913-2918.*

Shimizu, Hiroyuki et al, "Characterization of molecular forms of probrain natriuretic peptide in numan plasma", Clinica Chimica Acta 334 (2003) 233-239.

Hughes, et al., *An immunoluminometric assay for N-terminal pro-brain natriuretic peptide: development of a test for left ventricular dysfunction*, Clinical Science, 96:373-380 (1999).

* cited by examiner

*Primary Examiner*—Mark L Shibuya
*Assistant Examiner*—James L Grun (74) *Attorney, Agent, or Firm*—McDonnell Boehnen Hulbert & Berghoff LLP (57) ABSTRACT

The present invention concerns an immunological test for determining NT-proBNP comprising at least two antibodies to NT-proBNP, wherein at least one of the antibodies to NT-proBNP is a monoclonal antibody. One of these antibodies is directed at least against parts of the epitope of NT-proBNP comprising the amino acids 38 to 50. In addition, one of these antibodies is directed at least against parts of the epitope of NT-proBNP comprising the amino acids 1 to 37 or 43 to 76. The epitope recognized by the antibodies can slightly overlap.

33 Claims, 5 Drawing Sheets

Fig. 5 ized to US 7,507,550 B2

ANALYTICAL SANDWICH TEST FOR DETERMINING NT-PROBNP

BACKGROUND OF THE INVENTION

The present invention concerns an analytical sandwich test, in particular a test element and in particular in the form of an immunochromatographic test strip using the sandwich principle to determine N-terminal pro-brain natriuretic peptide (NT-proBNP).

NT-proBNP is a very promising marker for the diagnosis and management of heart failure. At present, the only NT-proBNP test that is available on the in-vitro diagnostic market is the fully automated Elecsys® NT-proBNP test from Roche Diagnostics which is based on a sandwich reaction with electrochemiluminescence detection. This test is designed to be used in large central laboratories and in addition to liquid reagents that have to be exactly dosed, requires a relatively complex instrument to dose the liquids and to detect the luminescence signal in order to carry out the test. A simple to use, rapid test for NT-proBNP which if needed can be evaluated visually without an evaluation instrument is presently not on the market.

In patients with acute respiratory distress it is advantageous to carry out a NT-proBNP determination as rapidly as possible in order to exclude or diagnose heart failure as a cause of the dyspnoea and to initiate appropriate treatment. Since the Elecsys® NT-proBNP test can only be carried out in a central laboratory, it is difficult to rapidly determine NT-proBNP outside the routine times. Hence, it would be particularly advantageous for the emergency ward if a rapid test were available which could be carried out directly in the emergency ward outside of routine times. This rapid test should, however, ensure the same reference ranges and cut-offs as the reference method in the central laboratory (Elecsys® NT-proBNP) in order to enable a good comparability of the results independently of the type of test that is actually carried out.

The polyclonal antibodies (PAB) used in the Elecsys® NT-proBNP test recognize a very special fraction of NT-proBNP ("native" NT-proBNP; see International Patent Application PCT/EP2004/005091 dated May 12, 2004 from Klemt et al.; according to this the test recognizes the epitopes of NT-proBNP comprising the amino acids 1-21 (AA 1-21) and 39-50 (AA 39-50)). However, it has turned out that these polyclonal antibodies are unsuitable for NT-proBNP rapid tests that use particulate labels such as colloidal gold as a label since they exhibit a high undesired variability in the signal generation due to physico-chemical interactions with the components of the rapid test (such as the support materials, matrices, etc.). This results in considerable fluctuations in the quality of the test from batch to batch.

SUMMARY OF THE INVENTION

It is against the above background that the present invention provides certain unobvious advantages and advancements over the prior art. In particular, the inventors have recognized a need for improvements in rapid analytical tests for determining NT-proBNP, which can be reproducibly manufactured and has a good correlation to the laboratory method.

In accordance with one embodiment of the present invention, an immunological test for determining NT-proBNP is provided comprising at least two antibodies to NT-proBNP, wherein at least one of the antibodies to NT-proBNP is a monoclonal antibody. One of these antibodies is directed at least against parts of the epitope of NT-proBNP comprising the amino acids 38 to 50. In addition, one of these antibodies is directed at least against parts of the epitope of NT-proBNP comprising the amino acids 1 to 37 or 43 to 76. The epitope recognized by the antibodies can slightly overlap.

These and other features and advantages of the present invention will be more fully understood from the following detailed description of the invention taken together with the accompanying claims. It is noted that the scope of the claims is defined by the recitations therein and not by the specific discussion of features and advantages set forth in the present description.

BRIEF DESCRIPTION OF THE DRAWINGS

The following detailed description of the embodiments of the present invention can be best understood when read in conjunction with the following drawings, where like structure is indicated with like reference numerals and in which.

Skilled artisans appreciate that elements in the figures are illustrated for simplicity and clarity and have not necessarily been drawn to scale. For example, the dimensions of some of the elements in the figures may be exaggerated relative to other elements to help improve understanding of the embodiment(s) of the present invention.

DETAILED DESCRIPTION OF EMBODIMENTS OF THE INVENTION

The inventive solution for producing an immunological test in a sandwich format in accordance with one embodiment of the present invention and, in particular, a rapid test which correlates well with the Elecsys® reference method uses a combination of antibodies comprising at least two antibodies to NT-proBNP, where at least one antibody is a monoclonal antibody (MAB). Another antibody of the sandwich test according to an embodiment of the present invention can either also be a MAB or a polyclonal antibody (PAB). In this connection one of these antibodies (abbreviated AB) is directed at least against parts of the epitope of NT-proBNP comprising amino acids 38 to 50 (in the following also abbreviated to AB (38-50) or MAB (38-50) or PAB (38-50)). At least one additional antibody is directed at least against parts of the epitope of NT-proBNP comprising amino acids 1 to 37 or 43 to 76 (in the following abbreviated to AB (1-37) or AB (43-76) or MAB (1-37) or MAB (43-76) or PAB (1-37) or PAB (43-76)). The epitopes recognized by the antibodies can slightly overlap, typically by less than 5 amino acids, more typically by less than 2 amino acids.

A combination of antibodies is typical comprising at least one polyclonal antibody (PAB) and one monoclonal antibody (MAB) (so-called PAB/MAB combination) to NT-proBNP.

The term PAB (X-Y) as used herein means a polyclonal antibody which is directed against the epitope of NT-proBNP comprising the amino acids X to Y. MAB (X-Y) is a corresponding monoclonal antibody. AB (X-Y) generally denotes an antibody (e.g., PAB or MAB) which is directed against the epitope of NT-proBNP comprising the amino acids X to Y.

MAB a.b.c. (X-Y) is a monoclonal antibody directed against the epitope of NT-proBNP comprising the amino acids X to Y which is obtained from a deposited cell line a.b.c.

In order to guarantee a reproducible quality of the antibody-label conjugate, the MAB is typically immobilized on a particulate label, in particular on a gold label. Other suitable particulate labels are for example coloured latices, other metal sol labels, polymer labels or semiconductor nanocrystals (so-called quantum dots). The MAB-label conjugate is typically provided on the rapid test device in such a manner that it can be detached from it by the sample liquid, for example by impregnating suitable support materials such as fleeces, membranes, etc. It is, however, also possible to add the MAB-label conjugate as a solution to the rapid test.

The PAB which is typically obtained by immunizing mammals, in particular sheep, goats or rabbits, is typically provided in the rapid test as a biotin derivative and can be bound to an avidin or streptavidin detection line. However, it also possible to directly immobilize the PAB in the rapid test device, for example in the form of a detection line on a suitable chromatography membrane.

According to an embodiment of the present invention, it is also possible although less typical, to use the labelled AB, in particular the labelled MAB, and the second antibody, in particular the second MAB or PAB in solution or in solutions for the rapid test. A binding partner which can capture the appropriately labelled AB is then located in a detection zone on the test device and thus binds the sandwich complex comprising first antibody, analyte and second antibody to a solid phase of the rapid test.

The MAB used according to an embodiment of the present invention does not necessarily have to recognize the epitope (AA 1-21) that is detected in the reference system (Elecsys® test) in order to ensure good correlation with the reference test: the antibody combinations and, in particular, the MAB/PAB combinations MAB 17.3.1 (13-16)/PAB (39-50) and MAB 18.4.34 (27-31)/PAB (39-50) correlate well with the Elecsys® reference system which uses polyclonal antibodies to the epitopes AA 1-21 and AA 39-50 of NT-proBNP (PAB (1-21) and PAB (39-50)). Other useful combinations include MAB 17.3.1 (13-16)/PAB (38-42) and MAB 18.4.34 (27-31)/PAB (38-42).

The polyclonal antibodies such as PAB (1-21) and PAB (39-50) can be obtained, characterized and identified by methods known to a person skilled in the art especially in analogy to example 2 of WO 00/45176.

The monoclonal antibodies such as MAB (38-42) and MAB (44-50) can be obtained, characterized and identified by methods known to a person skilled in the art especially in analogy to example 3 of WO 00/45176 or example 3 of the International Patent Application PCT/EP2004/005091 dated May 12, 2004 (Klemt et al.).

The antibodies are labelled for example with gold or other labels, biotin, etc. by methods known to a person skilled in the art (cf., also example 2 in WO 00/45176 and example 2 of the International Patent Application PCT/EP2004/005091 dated May 12, 2004 by Klemt et al.). Labelling with gold is, for example, described in detail in EP-A 0 898 170.

In particular, the typical monoclonal antibodies MAB 17.3.1 (13-16), MAB 16.1.39 (38-42), MAB 18.29.23 (64-67) and MAB 18.4.34 (27-31) can be obtained according to example 3 of the International Patent Application PCT/EP2004/005091 dated May 12, 2004 by Klemt et al. Corresponding cell lines are deposited at the "Deutsche Sammlung von Mikroorganismen und Zellkulturen GmbH (DSZM) (accession numbers of the depository and date of deposition: DSM ACC2591 May 7, 2003 for MAB 17.3.1 (13-16); DSM ACC2590 May 7, 2003 for MAB 16.1.39 (38-42); DSM ACC2593 May 7, 2003 for MAB 18.29.23 (64-67) and DSM ACC2592 May 7, 2003 for MAB 18.4.34 (27-31). Combination of these monoclonal antibodies may be useful in a sandwich assay for detecting NT-proBNP, including MAB 16.1.39 (38-42) and MAB 18.4.34 (27-31).

The combination of MAB 18.4.34 (27-31)/PAB (39-50) results in a relatively good correlation with the reference test as does the combination MAB 17.3.1 (13-16)/PAB (39-50) (see also example 2).

In addition the combination MAB 18.4.34 (27-31)/PAB (39-50) proved to be particularly advantageous for the test according to an embodiment of the present invention: this combination enabled a function curve to be adapted that is particularly suitable for rapid tests (see example 3). In comparison, the combination MAB 17.3.1 (13-16)/PAB (39-50) exhibited a poorer test sensitivity.

In order that the invention may be more readily understood, reference is made to the following examples, which are intended to illustrate the invention, but not limit the scope thereof.

EXAMPLES

Example 1

Preparation of a Test Device for Determining NT-proBNP from Whole Blood

The test device (FIG. 1) consists of a support material (5) on which a sample application zone (1), an erythrocyte separation zone (2), a detection zone (3) and a suction zone (4) are mounted. A sample application matrix (6) which partially overlaps an erythrocyte separation zone (7) is located in the sample application zone (1). The erythrocyte separation matrix (7) in turn slightly overlaps the detection matrix (8) (detection zone) on which an immobilized substance is applied in the form of a line (9). A suction matrix (10) slightly overlaps the detection matrix (8). All reagents that are necessary to form a complex with the analyte to be detected are accommodated in the sample application matrix (6). For example, the sample application zone can be composed of two fleeces on top of one another where the first ("gold fleece") is impregnated with a gold-labelled antibody to NT-proBNP (MAB 18.4.34 (27-31)) and the second fleece ("biotin fleece") contains a biotinylated antibody to NT-proBNP (PAB (39-50)). A line (9) made of streptavidin is applied within the detection zone.

Figure 1:
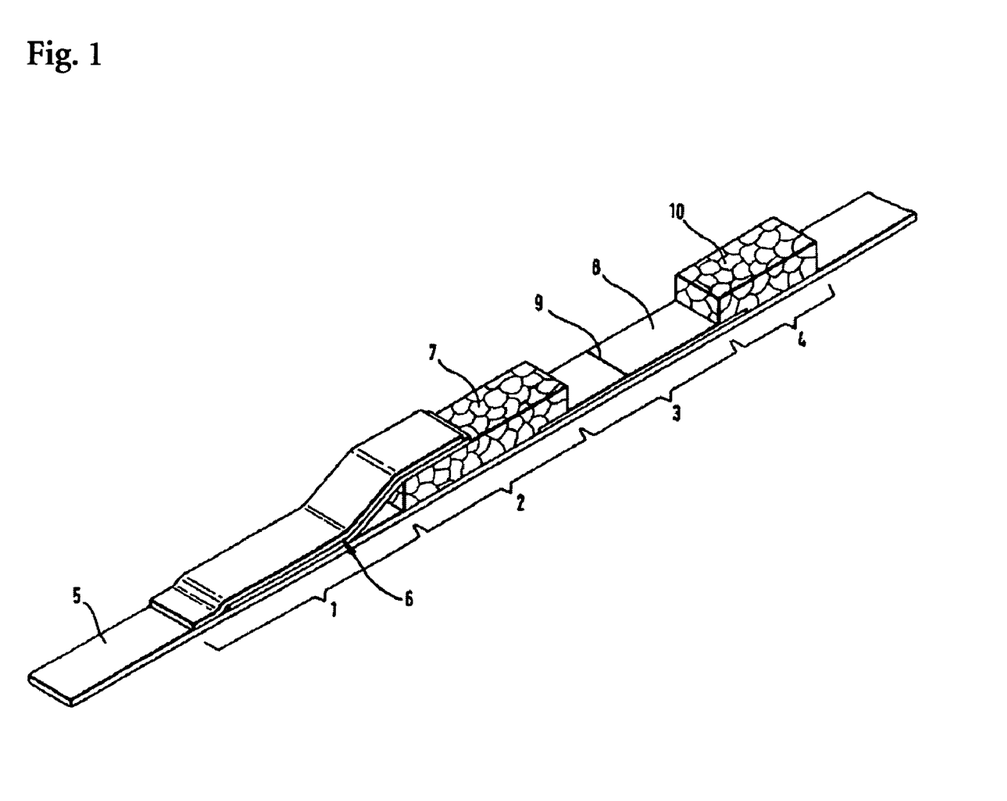
FIG. 1 shows a diagram of a rapid test device according to one embodiment of the present invention in the form of an immunochromatographic test strip.

A polyester foil (Pütz) of 350 µm thickness is used as the support layer (5). A polyester fleece (Roche Diagnostics) of 360 µm thickness is used as the "gold fleece" or "biotin fleece" of the sample application matrix (6). A glass fibre fleece (Roche Diagnostics) of 1.8 mm thickness is used as an erythrocyte separation matrix (7). A nitrocellulose membrane (Sartorius) of 140 µm thickness is used as the detection matrix (8). A glass fibre fleece (Roche Diagnostics) of 1.8 mm thickness is used as the suction matrix (10). The individual components (6, 7, 8, 10) are glued slightly overlapping on the support layer (5) by means of hot-melt adhesive as shown in FIG. 1.

The impregnation formulation of the "gold and biotin fleeces" is:

"biotin fleece": 100 mM Hepes pH 7.4, 0.1% Tween®, 20 µg/ml biotinylated PAB (39-50)

"gold fleece": 100 mM Hepes pH 7.4, OD 4 MAB 18.4.34 (27-31) gold conjugate

Example 2

Figure 2:
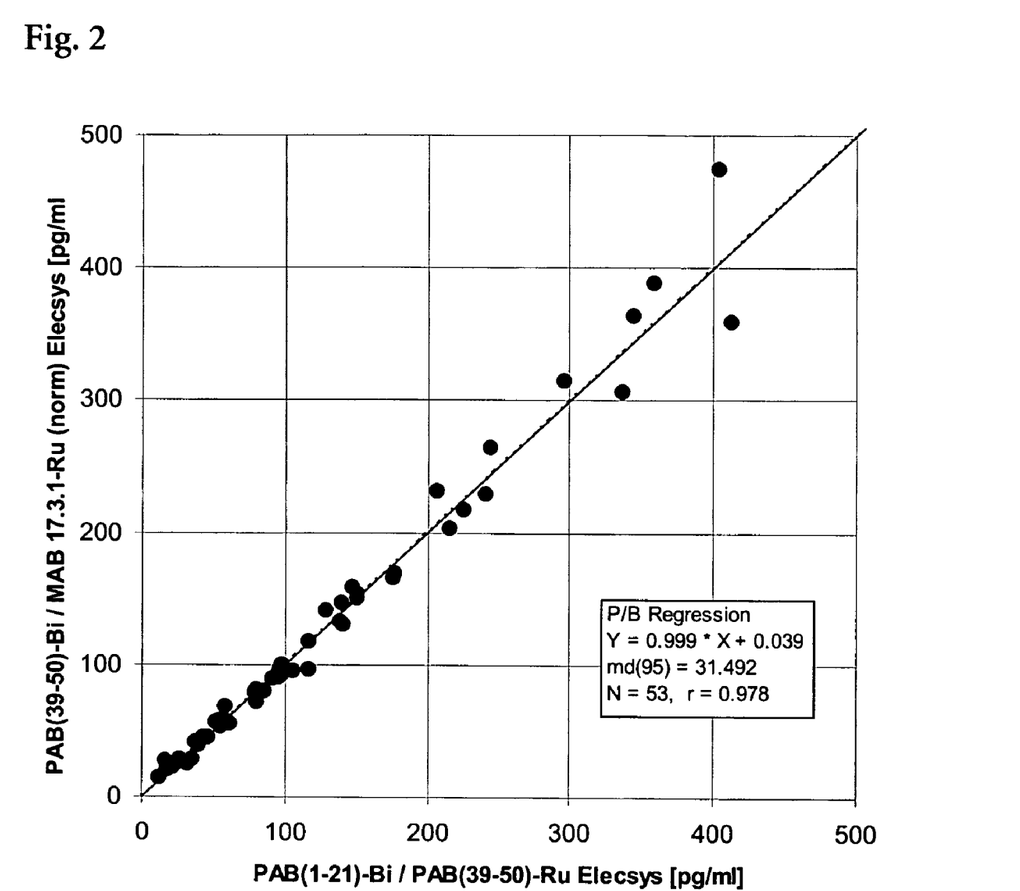
FIG. 2 shows the correlation of the antibody combination MAB 17.3.1 (13-16)/PAB (39-50) in the Elecsys® wet test format with the Elecsys® reference method PAB (1-21)/PAB (39-50)
Figure 3:
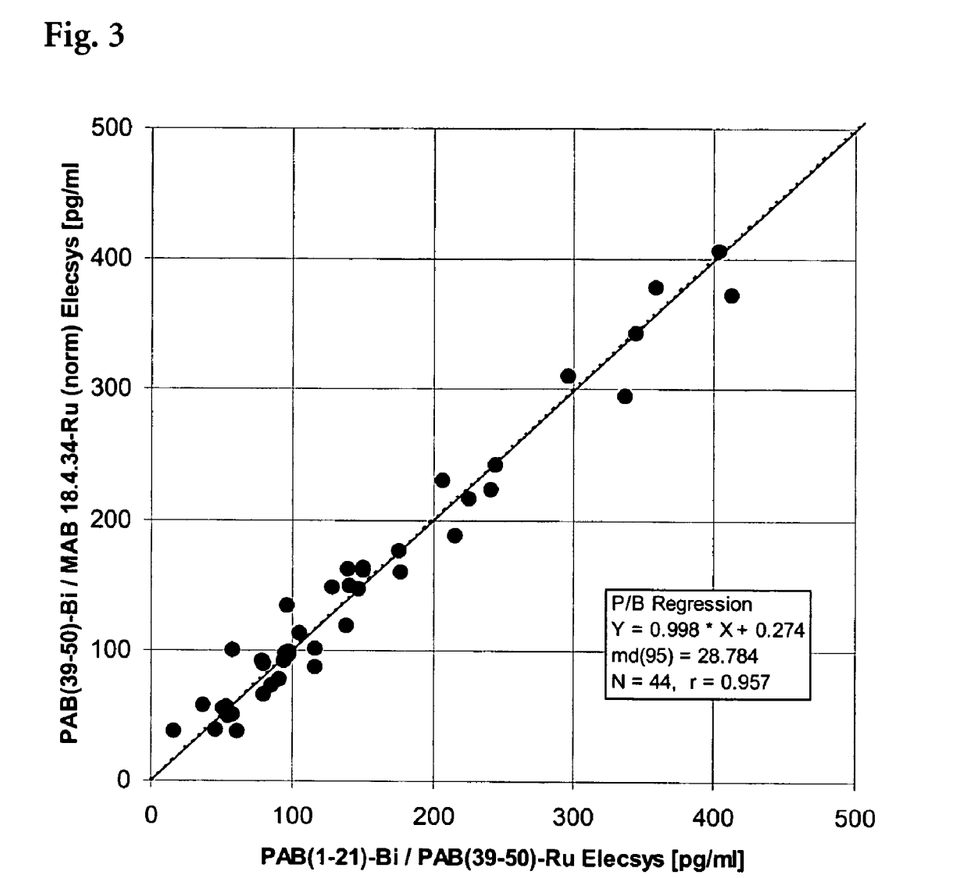
FIG. 3 shows the correlation of the antibody combination MAB 18.4.34 (27-31)/PAB (39-50) in the Elecsys® wet test format with the Elecsys® reference method PAB (1-21)/PAB (39-50)

Correlation of the Epitope/Antibody Combination MAB 17.3.1 (13-16)/PAB (39-50) and MAB 18.4.34 (27-31)/PAB (39-50) in the Elecsys® Format to the Elecsys® NT-proBNP Test Kit (cf., FIGS. 2 and 3)

The correlation of the MAB/PAB combinations MAB 17.3.1 (13-16)/PAB (39-50) and MAB 18.4.34 (27-31)/PAB (39-50) to the Elecsys® test kit (PAB (1-21)/PAB (30-50)) was examined in an electrochemiluminescence immunoassay on an Elecsys® 2010 (Roche Diagnostics). For this the PAB (39-50) was used as a biotinylated capture reagent and ruthenylated $F(ab')_2$ fragments of the MABs were used as the detection reagent. 20 µl sample or standard material was in each case incubated with 75 µl of the two antibody reagents for 9 minutes at 37° C. Afterwards, 35 µl streptavidin-coated magnetic polystyrene particles were added and it was incubated for a further 9 minutes at room temperature. The electroluminescence signal of an aliquot of the incubation solution was measured routinely on the Elecsys® 2010 and converted into a concentration signal by means of a standard curve.

Clinical samples from patients with cardiac failure were now measured with the two MAB/PAB test variants and the Elecsys® kit. The results are shown in FIGS. 2 and 3. A very good correlation to the Elecsys® kit (r=0.978 and r=0.957) was obtained with both MAB/PAB variants.

Example 3

Function Curve of an NT-proBNP Test Strip with Two Different MAB/PAB Combinations An NT-proBNP test strip was prepared according to Example 1. The following impregnation formulation for the reagent fleeces was used:

"biotin fleece": 100 mM Hepes pH 7.4, 0.1% Tween®, 20 µg/ml biotinylated PAB (39-50)

Figure 4:
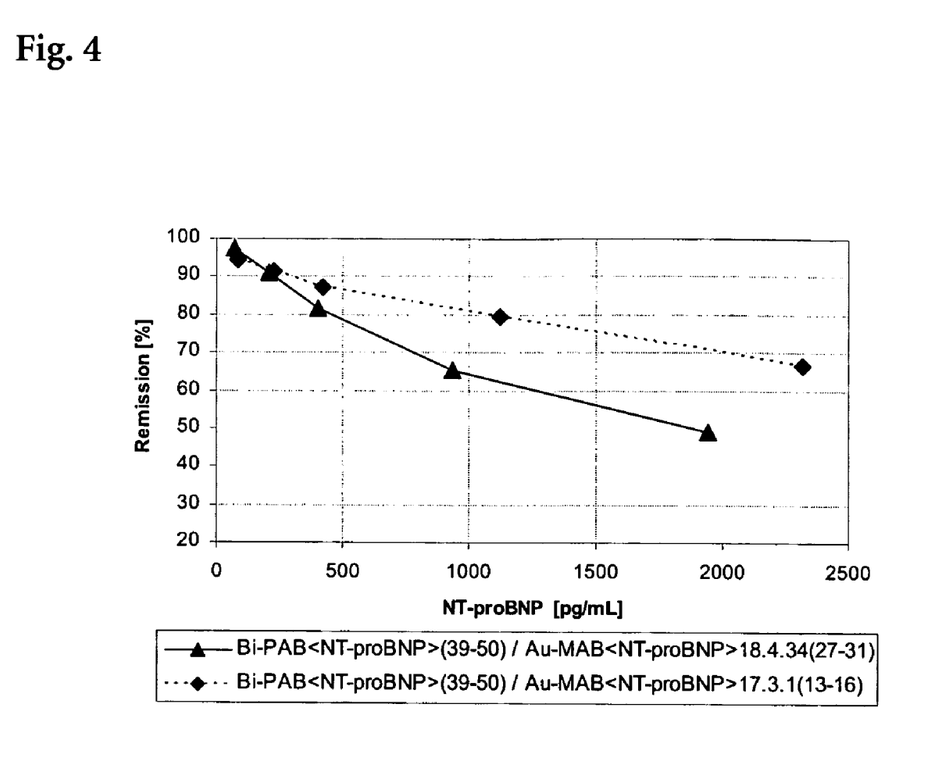
FIG. 4 shows function curves of NT-proBNP test strips according to Example 1 with different antibody combinations.

"gold fleece": 100 mM Hepes pH 7.4, OD 4 MAB 18.4.34 (27-31) or MAB 17.3.1 (13-16) gold conjugate Heparinized blood samples from healthy donors were spiked with sera containing NT-proBNP from heart failure patients and aliquoted. 150 µl of the spiked blood samples was pipetted onto the test strips and measured in a CARDIAC Reader® (Roche Diagnostics). The reaction time after sample detection was 12 minutes. In order to determine the NT-proBNP concentration of the samples, plasma was centrifuged from one aliquot and measured with an Elecsys® NT-proBNP kit (Roche Diagnostics). Function curves obtained in this manner of the two test strip variants MAB 17.3.1 (13-16)/PAB (39-50) and MAB 18.4.34 (27-31)/PAB (39-50) are shown in FIG. 4. The variant MAB 18.4.34 (27-31)/PAB (39-50) has a considerably steeper standard curve and is thus a more sensitive test.

Example 4

Figure 5:
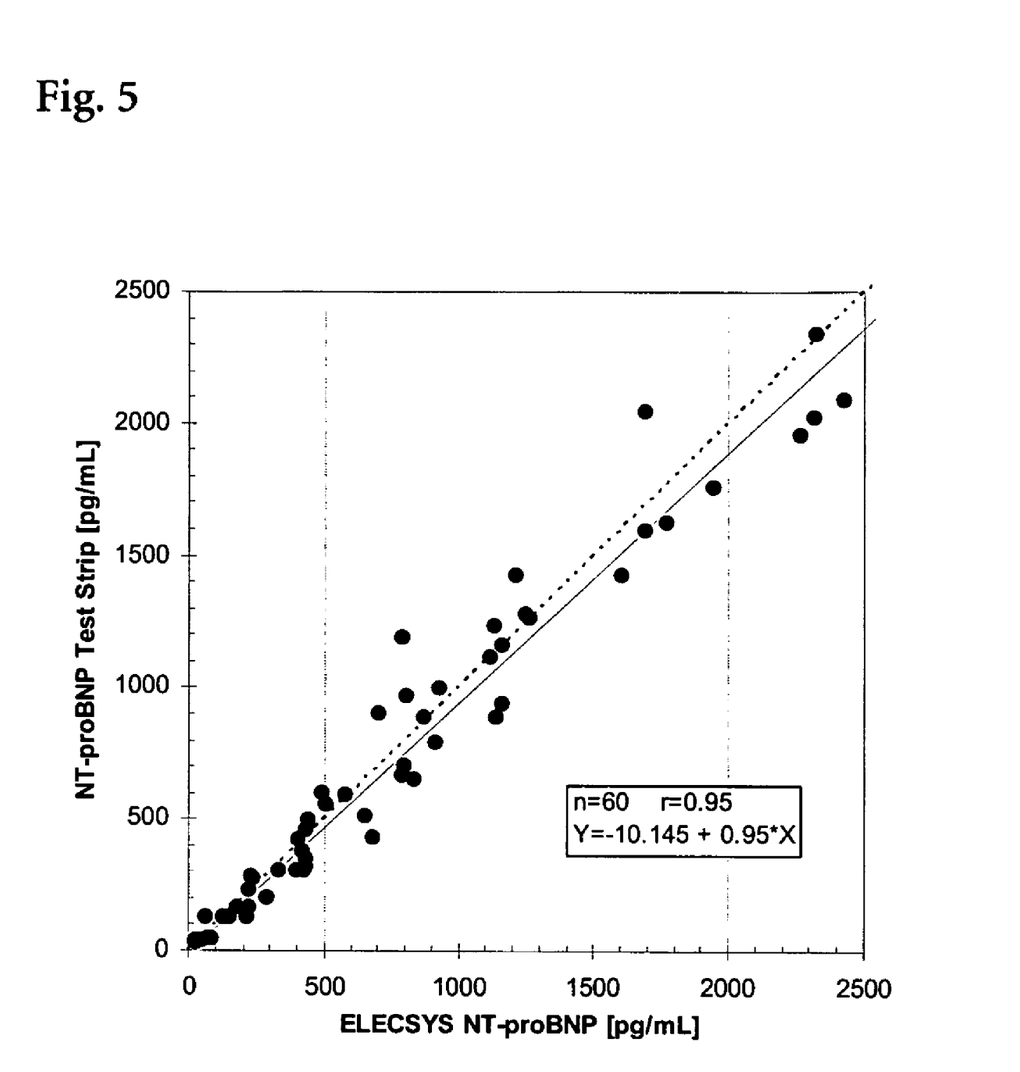
FIG. 5 shows the correlation of an NT-proBNP test strip with the antibody combination: Au-MAB 18.4.34 (27-31)/Bi-PAB (39-50) to the Elecsys® NT-proBNP test kit.

Correlation of an NT-proBNP Test Strip with the AB Combination: Au-MAB 18.4.34 (27-31)/Bi-PAB (39-50) to the Elecsys® NT-proBNP Test Kit Sera containing NT-proBNP from patients with cardiac failure were added to heparinized blood samples from healthy donors and aliquoted. 150 µl of these "spiked" blood samples was pipetted onto the test strips and measured in a CARDIAC Reader® (Roche Diagnostics) according to the standard method. Plasma was centrifuged from the same sample and measured with the Elecsys® NT-proBNP kit on an Elecsys® 1010 analytical system (Roche Diagnostics). 60 samples were prepared in this manner and measured with both systems. FIG. 5 shows the measured values for both systems. The correlation is very good at r=0.95.

It is noted that terms like "preferably", "commonly", and "typically" are not utilized herein to limit the scope of the claimed invention or to imply that certain features are critical, essential, or even important to the structure or function of the claimed invention. Rather, these terms are merely intended to highlight alternative or additional features that may or may not be utilized in a particular embodiment of the present invention.

For the purposes of describing and defining the present invention it is noted that the term "substantially" is utilized herein to represent the inherent degree of uncertainty that may be attributed to any quantitative comparison, value, measurement, or other representation. The term "substantially" is also utilized herein to represent the degree by which a quantitative representation may vary from a stated reference without resulting in a change in the basic function of the subject matter at issue.

Having described the invention in detail and by reference to specific embodiments thereof, it will be apparent that modifications and variations are possible without departing from the scope of the invention defined in the appended claims. More specifically, although some aspects of the present invention are identified herein as preferred or particularly advantageous, it is contemplated that the present invention is not necessarily limited to these preferred aspects of the invention.

What is claimed is:

1. An immunological test device for determining N-terminal pro-brain natriuretic peptide (NT-proBNP) comprising:
    a sample application zone for receiving a liquid sample;
    a monoclonal antibody directed against an epitope of NT-proBNP comprising amino acids 27 to 31, produced by hybridoma cell line 18.4.34 deposited with DSMZ-Deutsche Sammlung von Mikroorganismen und Zellkulturen GmbH under accession number DSM ACC2592, or a monoclonal antibody directed against an epitope of NT-proBNP comprising amino acids 13 to 16, produced by hybridoma cell line 17.3.1 deposited with DSMZ-Deutsche Sammlung von Mikroorganismen und Zellkulturen GmbH under accession number DSM ACC2591,
    a polyclonal antibody selected from polyclonal antibodies directed against epitopes of NT-proBNP comprising amino acids 39 to 50 or amino acids 38 to 42; and
    a detection zone in fluid communication with the sample application zone for binding a complex comprising NT-proBNP, the monoclonal antibody and the polyclonal antibody.

2. The immunological test device of claim 1, wherein said sample application zone comprises a matrix material, and wherein the matrix material is impregnated with the monoclonal antibody and the polyclonal antibody.

3. An immunological test device for determining N-terminal pro-brain natriuretic peptide (NT-proBNP) comprising:
a sample application zone for receiving a liquid sample;
a first monoclonal antibody directed against an epitope of NT-proBNP comprising amino acids 27 to 31, produced by hybridoma cell line 18.4.34 deposited with DSMZ-Deutsche Sammlung von Mikroorganismen und Zellkulturen GmbH under accession number DSM ACC2592,
a second monoclonal antibody directed against an epitope of NT-proBNP comprising amino acids 38 to 42, produced by hybridoma cell line 16.1.39 deposited with DSMZ-Deutsche Sammlung von Mikroorganismen und Zellkulturen GmbH under accession number DSM ACC2590; and
a detection zone in fluid communication with the sample application zone for binding a complex comprising NT-proBNP and the first and second monoclonal antibodies.

4. The immunological test device of claim 3, wherein said sample application zone comprises a matrix material, and wherein said matrix material is impregnated with the first monoclonal antibody and the second monoclonal antibody.

5. The immunological test device of claim 1 or 3, wherein said sample application zone comprises a matrix material.

6. The immunological test device of claim 5, wherein said matrix comprises at least two fleece structures.

7. The immunological test device of claim 6, wherein said fleece structure is polyester.

8. The immunological test device of claim 1 or 3, wherein said detection zone comprises a nitrocellulose membrane.

9. The immunological test device of claim 1 or 3, wherein said detection zone comprises at least one immobilized immunochemical component.

10. The immunological test device of claim 9, wherein said immobilized immunochemical component is applied on said detection zone in the form of a line.

11. The immunological test device of claim 9, wherein said immobilized immunochemical component comprises streptavidin or polystreptavidin.

12. The immunological test device of claim 9, wherein said immobilized immunochemical component comprises an antigen or antigen analogue.

13. The immunological test device of claim 1 or 3 further comprising an erythrocyte separation zone located downstream from said sample application zone.

14. The immunological test device of claim 13, wherein said erythrocyte separation zone comprises glass fibers.

15. The immunological test device of claim 13, wherein said sample application zone is in fluid communication with or at least partially overlaps said erythrocyte separation zone.

16. The immunological test device of claim 13, wherein said erythrocyte separation zone is in fluid communication with or at least partially overlaps said detection zone.

17. The immunological test device of claim 1 or 3 further comprising a suction zone located downstream from said detection zone.

18. The immunological test device of claim 17, wherein said suction zone is in fluid communication with or at least partially overlaps said detection zone.

19. The immunological test device of claim 1 or 3 further comprising a support material.

20. The immunological test device of claim 19, wherein said support material comprises a polyester foil.

21. The immunological test device of claim 1 or 3, wherein the test device is an immunochromatographic test device.

22. The immunological test device of claim 21, wherein one of the antibodies is present as an antibody-gold conjugate.

23. The immunological test device of claim 21, wherein one of the antibodies is present as a biotinylated antibody.

24. A method for detecting N-terminal pro-brain natriuretic peptide (NT-proBNP) comprising:
providing the immunological test device of claim 1;
adding a biological sample suspected of containing NT-proBNP to the test device; and
determining presence or amount of NT-proBNP in the sample that binds to both the monoclonal antibody and the polyclonal antibody.

25. A method for detecting N-terminal pro-brain natriuretic peptide (NT-proBNP) comprising:
providing the immunological test device of claim 3;
adding a biological sample suspected of containing NT-proBNP to the test device; and
determining presence or amount of NT-proBNP in the sample that binds to both the first and second monoclonal antibodies.

26. A method for determining N-terminal pro-brain natriuretic peptide (NT-proBNP) in a patient sample, the method comprising:
(a) contacting a patient sample with (1) a monoclonal antibody directed against an epitope of NT-proBNP comprising amino acids 27 to 31, produced by hybridoma cell line 18.4.34 deposited with DSMZ-Deutsche Sammlung von Mikroorganismen und Zellkulturen GmbH under accession number DSM ACC2592, or a monoclonal antibody directed against an epitope of NT-proBNP comprising amino acids 13 to 16, produced by hybridoma cell line 17.3.1 deposited with DSMZ-Deutsche Sammlung von Mikroorganismen und Zellkulturen GmbH under accession number DSM ACC2591, and (2) a polyclonal antibody selected from polyclonal antibodies directed against epitopes of NT-proBNP comprising amino acids 39 to 50, amino acids 38 to 42, or amino acids 44 to 50; and
(b) forming a complex comprising NT-proBNP from the sample, the monoclonal antibody produced by hybridoma cell line 18.4.34 or the monoclonal antibody produced by hybridoma cell line 17.3.1, and the polyclonal antibody; and
(c) detecting the complex, thereby determining NT-proBNP in the sample.

27. The method of claim 26 wherein the (1) the monoclonal antibody produced by hybridoma cell line 18.4.34 or the monoclonal antibody produced by hybridoma cell line 17.3.1 is attached to a label.

28. The method of claim 26 wherein the polyclonal antibody is bound to a support.

29. The method of claim 26 wherein the sample is a serum sample.

30. A method for determining N-terminal pro-brain natriuretic peptide (NT-proBNP) in a patient sample, the method comprising:
(a) contacting a patient sample with a first monoclonal antibody directed against an epitope of NT-proBNP comprising amino acids 27 to 31, produced by hybridoma cell line 18.4.34 deposited with DSMZ-Deutsche Sammlung von Mikroorganismen und Zellkulturen GmbH under accession number DSM ACC2592, and a second monoclonal antibody directed against an epitope of NT-proBNP comprising amino acids 38 to 42, produced by hybridoma cell line 16.1.39 deposited with DSMZ-Deutsche Sammlung von Mikroorganismen und Zellkulturen GmbH under accession number DSM ACC2590;
(b) forming a complex comprising NT-proBNP from the sample, and the first and second monoclonal antibodies; and
(c) detecting the complex, thereby determining NT-proBNP in the sample.

31. The method of claim 30 wherein either the first or second monoclonal antibody is attached to a label.

32. The method of claim 30 wherein either the first or second monoclonal antibody is bound to a support.

33. The method of claim 30 wherein the sample is a serum sample.

* * * * *